(12) United States Patent
Haubennestel et al.

(10) Patent No.: US 7,655,815 B2
(45) Date of Patent: Feb. 2, 2010

(54) BIURET COMPOUNDS FOR RHEOLOGY CONTROL

(75) Inventors: Karlheinz Haubennestel, Wesel (DE); Ulrich Orth, Wesel (DE); Matthias Pickave, Mulheim/Ruhr (DE); Stefan Moessmer, Wesel (DE); Daniela Betcke, Wesel (DE)

(73) Assignee: BYK-Chemie GmbH (DE)

( * ) Notice: Subject to any disclaimer, the term of this patent is extended or adjusted under 35 U.S.C. 154(b) by 498 days.

(21) Appl. No.: 11/714,687

(22) Filed: Mar. 6, 2007

(65) Prior Publication Data

US 2007/0225451 A1 Sep. 27, 2007

(30) Foreign Application Priority Data

Mar. 8, 2006 (DE) .................. 10 2006 010 721

(51) Int. Cl.
 C07C 271/06 (2006.01)
 C07C 275/00 (2006.01)
(52) U.S. Cl. ............ 560/158; 564/38; 525/440.02
(58) Field of Classification Search .......... 560/158; 564/38; 525/440.02
 See application file for complete search history.

(56) References Cited

U.S. PATENT DOCUMENTS 3,856,830 A * 12/1974 Kuehn .................. 554/91
4,019,972 A * 4/1977 Faust .................. 430/283.1

FOREIGN PATENT DOCUMENTS

EP 1048681 A2 11/2000
EP 1593700 A1 11/2005

\* cited by examiner

*Primary Examiner*—Shailendra Kumar
(74) *Attorney, Agent, or Firm*—Schwegman, Lundberg & Woessner, P.A.

(57) ABSTRACT

The invention relates to biuret compounds of the idealized general formula

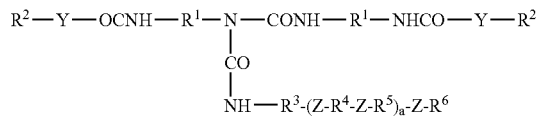

in which $R^1$ is a $(C_1-C_{22})$-alkylene, $(C_3-C_{22})$-alkenylene, $(C_5-C_{15})$-cycloalkylene, arylene, $(C_7-C_{12})$-aralkylene, a polyoxyalkylene radical or is a polyester radical, $R^2$ is a $(C_1-C_{22})$-alkyl, hydroxy-$(C_1-C_{22})$-alkyl, $(C_3-C_{18})$-alkenyl, aryl, $(C_7-C_{12})$-aralkyl, or $(C_5-C_{12})$-cycloalkyl radical, a hydroxy-, $(C_1-C_{22})$-alkoxy-, $(C_5-C_{12})$-cycloalkoxy-, or $(C_7-C_{12})$-aralkoxy-polyoxyalkylene radical, or a polyester radical prepared starting from a $(C_1-C_{22})$-alkanol, $(C_5-C_{12})$-cycloalkanol, or $(C_7-C_{12})$-aralkanol or from a $(C_1-C_{22})$-alkoxy-, $(C_6-C_{12})$-cycloalkoxy-, or $(C_7-C_{12})$-aralkoxy-polyoxyalkylene, Y stands for identical or different radicals O, NH, CO—NH—NH or NH—NH—CO, $R^3$, $R^4$ and $R^5$ independently of one another are a $(C_2-C_{40})$-alkylene, $(C_3-C_{40})$-alkenylene, $(C_5-C_{40})$-cyclo-alkylene, arylene, $(C_7-C_{40})$-aralkylene or polyoxy-alkylene radical or are a polyester radical, $R^6$ is a $(C_1-C_{30})$-alkyl, $(C_3-C_{22})$-alkenyl, hydroxyalkyl and hydroxyalkenyl, $(C_4-C_{13})$-cycloalkyl, aryl or $(C_7-C_{12})$-aralkyl radical, Z stands for one or more of the following groups COO, OCO, NHCO, CONH, NHCOO, OOCNH and NHCONH, and a is a number from 1 to 19, and also to processes for preparing them and to their use for rheology control and for thixotroping coating systems, as anti-sag agents and/or as anti-settling agents.

17 Claims, No Drawings

BIURET COMPOUNDS FOR RHEOLOGY CONTROL

RELATED APPLICATION

This application claims priority under 35 U.S.C. 119 to German Application No. 10 2006 010 721.7, filed Mar. 8, 2006, which application is incorporated herein by reference and made a part hereof.

The invention relates to biuret compounds, to processes for preparing them and to their use as rheology control agents for coating systems such as, for example, solvent-borne, solvent-free and aqueous coating materials, PVC plastisols, epoxy-based coatings and those based on unsaturated polyester resins.

In order to control the rheology of liquid coating systems it is common to use silicas, hydrogenated castor oil or organically modified bentonites, as described, for example, in U.S. Pat. Nos. 4,208,218; 4,410,364 and 4,412,018. Furthermore, polyamide waxes are widely employed. Specifically in the field of polyamides and polyamide esters, there exist numerous patents, such as DE 69523221, EP 0528363, EP 0239419, U.S. Pat. Nos. 5,510,452 and 5,349,011.

Combinations of modified bentonites with polyamides, as described in EP 0509202 and DE 69704691, are also used.

A disadvantage of these substances is that they generally constitute dry solids or pastes which have to be opened up into a semi-finished product using solvents and shear forces and introduced into the liquid coating system by means of targeted temperature control. If these temperatures are not maintained, crystallites occur in the finished coating system and lead to defects in the coating. The general disadvantage of these systems is that they lead to clouding and haze in clear, transparent coatings.

Moreover, handling dry products which give rise to dust during processing is undesirable.

The polyamide esters are frequently liquid and are therefore much less effective than the inherently solid substances.

Other solutions for rheology control have been presented in EP 0 198 519. There an isocyanate is reacted with an amine in the presence of binders to form a urea which in very finely dispersed form forms acicular crystals. These binders thus modified are offered as rheology-controlling and sag-preventing binders, referred to as sag control agents.

The disadvantage of these products lies in the fact that they are always tied to these binders in which they have been prepared, and do not allow subsequent universal correction of completed coating materials.

EP 0 006 252 describes a process for preparing a thixotropic agent that removes some of the above disadvantages, describing urea urethanes which are prepared in aprotic solvents in the presence of LiCl by reaction of isocyanate adducts of polyamines. The disadvantage of the products thus prepared lies in the undefined structure of these urea urethanes, which is a consequence of the preparation process. In that process 1 mol of a diisocyanate is first reacted with 1 mol of a monoalcohol. This produces the desired NCO-functional monoadducts, but also non-NCO-functional diadducts. Furthermore, a certain fraction of monomeric diisocyanate remains unreacted. The fractions of these various compounds may fluctuate, depending on the reactivity of the NCO group and the reaction conditions, such as temperature and time. All of these adducts prepared in this way, however, contain relatively large amounts of unreacted diisocyanate, which on further reaction with polyamines leads to uncontrolled chain extension of the molecule. These products then exhibit a propensity towards precipitation phenomena or premature gelling and, accordingly, to the formation of what are called "seeds" in the binder. In DE 19919482 these disadvantages are circumvented by removal of the excess isocyanate. Those products, however, have the disadvantage that they yield stable solutions only in high-polarity solvents such as NMP, for example, with the assistance of alkali metal salts.

It is the object of the present invention to find a process which produces thixotropic agents of more defined structure and thereby ensures an improved effect profile and improved reproducibility of thixotroping.

Surprisingly it has been found that this can be achieved by means of biuret compounds which are preparable from uretdiones (component A) and monoamine-functional compounds (component B) and having the general structure A-B.

The invention accordingly provides biuret compounds of the idealized general formula

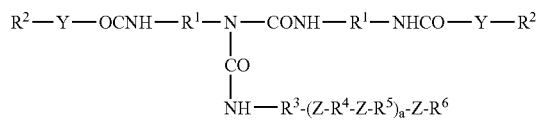

in which $R^1$ is a $(C_1-C_{22})$-alkylene, $(C_3-C_{22})$-alkenylene, $(C_5-C_{15})$-cycloalkylene, arylene, $(C_7-C_{12})$-aralkylene, a polyoxy-alkylene radical or is a polyester radical, $R^2$ is a $(C_1-C_{22})$-alkyl, hydroxy-$(C_1-C_{22})$-alkyl, $(C_3-C_{18})$-alkenyl, aryl, $(C_7-C_{12})$-aralkyl, or $(C_5-C_{12})$-cycloalkyl radical, a hydroxy-, $(C_1-C_{22})$-alkoxy-, $(C_5-C_{12})$-cycloalkoxy-, or $(C_7-C_{12})$-aralkoxy-polyoxyalkylene radical, or a polyester prepared starting from a $(C_1-C_{22})$-alkanol, $(C_5-C_{12})$-cycloalkanol, or $(C_7-C_{12})$-aralkanol or from a $(C_1-C_{22})$-alkoxy-, $(C_6-C_{12})$-cycloalkoxy-, or $(C_7-C_{12})$-aralkoxy-polyoxyalkylene, Y stands for identical or different radicals O, NH, CO—NH—NH or NH—NH—CO, $R^3$, $R^4$ and $R^5$ independently of one another are a $(C_2-C_{40})$-alkylene, $(C_3-C_{40})$-alkenylene, $(C_5-C_{40})$-cyclo-alkylene, arylene, $(C_7-C_{40})$-aralkylene or polyoxy-alkylene radical or are a polyester radical, $R^6$ is a $(C_1-C_{30})$-alkyl, $(C_3-C_{22})$-alkenyl, hydroxyalkyl and hydroxyalkenyl, $(C_4-C_{13})$-cycloalkyl, aryl or $(C_7-C_{12})$-aralkyl radical, Z stands for one or more of the following groups COO, OCO, NHCO, CONH, NHCOO, OOCNH and NHCONH, and a is a number from 1 to 19.

The definitions of the radicals $R^1$, $R^2$, $R^3$, $R^4$, $R^5$, $R^6$, Y and Z and also of the index a correspond to the above definitions in the context of this invention, irrespective of the compounds in which they feature. Preferred versions of these radicals are found in the respective subsections.

Where one or more of the radicals $R^1$, $R^2$, $R^3$, $R^4$ and/or $R^5$ contain a polyoxyalkylene fraction, these radicals, irrespective of the compounds in which they feature, are constructed preferably from ethylene oxide, propylene oxide and/or butylene oxide units, in random or blockwise arrangement, and, where appropriate, one or more of these units are substituted by styrene units. Particular preference is given to ethylene oxide radicals and propylene oxide radicals.

Where one or more of the radicals $R^1$, $R^2$, $R^3$, $R^4$ and/or $R^5$ comprise a polyester radical, these radicals, irrespective of the compounds in which they feature, are constructed preferably on the basis of one or more $(C_1-C_{18})$-hydroxycarboxylic acids or one or more lactones, such as β-propiolactone, δ-valerolactone, ε-caprolactone and ($C_1$-$C_6$)-alkyl-substituted ε-caprolactone.

$R^1$ is more preferably a hexamethylene radical.

$R^2$ is preferably a ($C_1$-$C_{22}$)-alkyl or a -alkoxypolyoxyalkylene radical.

The radicals $R^3$ and $R^5$ independently of one another are preferably a ($C_2$-$C_{18}$)-alkylene, ($C_7$-$C_1$)-aralkylene radical, more preferably a ($C_2$-$C_{12}$)-alkylene, ($C_7$-$C_{12}$)-aralkylene radical, very preferably a ($C_2$-$C_8$)-alkylene, ($C_7$-$C_9$)-aralkylene radical, such as a hexamethylene, octamethylene or m-xylylene radical, for example. The radicals $R^3$ and $R^5$ are preferably identical.

$R^4$ is a ($C_2$-$C_{40}$)-alkylene, ($C_3$-$C_{40}$)-alkenylene, ($C_5$-$C_{40}$)-cycloalkylene, arylene or ($C_7$-$C_{40}$)-aralkylene radical, preferably a ($C_{30}$-$C_{40}$)-alkylene, ($C_{30}$-$C_{40}$)-alkenylene, ($C_{30}$-$C_{40}$)-cycloalkylene, arylene, or ($C_{30}$-$C_{40}$)-aralkylene radical, such as, for example, the radical between the two carboxylic acid groups of dimer acid. $R^4$ is more preferably a $C_{34}$ radical.

$R^6$ is preferably a ($C_1$-$C_{30}$)-alkyl or a ($C_3$-$C_{22}$)-alkenyl radical, which may if appropriate be substituted by hydroxyl groups, more preferably a ($C_{12}$-$C_{30}$)-alkyl or a ($C_{12}$-$C_{22}$)-alkenyl radical and very preferably a ($C_{12}$-$C_{20}$)-alkyl or a ($C_{12}$-$C_{20}$)-alkenyl radical, such as a $C_{17}$ alkyl or a $C_{17}$ alkenyl radical, for example.

Z is more preferably NHCO and CONH.

The index a is a number from 1 to 19, more preferably from 2 to 7.

The invention also provides a process for preparing thixotropy-generating and sag-preventing biuret compounds of the general structure A-B, obtainable by reacting uretdiones of the idealized general formula (A)

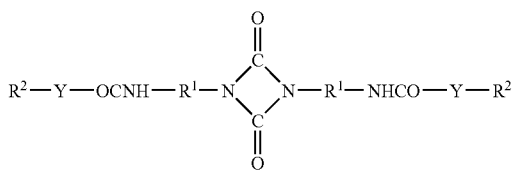

(A)

where $R^1$ is a ($C_1$-$C_{22}$)-alkylene, ($C_3$-$C_{22}$)-alkenylene, ($C_5$-$C_{15}$)-cycloalkylene, arylene, ($C_7$-$C_{12}$)-aralkylene, a polyoxyalkylene radical or is a polyester radical, $R^2$ is a ($C_1$-$C_{22}$)-alkyl, hydroxy-($C_1$-$C_{22}$)-alkyl, ($C_3$-$C_{18}$)-alkenyl, aryl, ($C_7$-$C_{12}$)-aralkyl, or ($C_5$-$C_{12}$)-cycloalkyl radical, a hydroxy-, ($C_1$-$C_{22}$)-alkoxy-, ($C_5$-$C_{12}$)-cycloalkoxy-, or ($C_7$-$C_{12}$)-aralkoxy-polyoxyalkylene radical, or a polyester prepared starting from a ($C_1$-$C_{22}$)-alkanol, ($C_5$-$C_{12}$)-cycloalkanol, or ($C_7$-$C_{12}$)-aralkanol or from a ($C_1$-$C_{22}$)-alkoxy-, ($C_6$-$C_{12}$)-cycloalkoxy-, or ($C_7$-$C_{12}$)-aralkoxy-polyoxyalkylene, Y stands for identical or different radicals O, NH, CO—NH—NH or NH—NH—CO, with monoamine-functional compounds of the idealized general structure (B)

(B)

where $R^3$, $R^4$ and $R^5$ independently of one another are a ($C_2$-$C_{40}$)-alkylene, ($C_3$-$C_{40}$)-alkenylene, ($C_5$-$C_{40}$)-cycloalkylene, arylene, ($C_7$-$C_{40}$)-aralkylene or polyoxy-alkylene radical or are a polyester radical, $R^6$ is a ($C_1$-$C_{30}$)-alkyl, ($C_3$-$C_{22}$)-alkenyl, hydroxyalkyl and hydroxyalkenyl, ($C_4$-$C_{13}$)-cycloalkyl, aryl or ($C_7$-$C_{12}$)-aralkyl radical, Z stands for one or more of the following groups COO, OCO, NHCO, CONH, NHCOO, OOCNH and NHCONH, and a is a number from 1 to 19.

In the preparation of the biuret compounds of the invention, of the general structure A-B, uretdione-containing polyisocyanates are first reacted, with retention of the uretdione moiety, with monoalcohols to form urethane-containing polymers, or with monoamines and/or alkanolamines and/or monohydrazides to form urea- and/or semicarbazide-containing polymers, and in a 2nd step, accompanied by opening of the uretdione ring, and with an amine-functional compound, the biuret compounds of the invention are prepared.

Uretdiones, as the skilled person is aware, are prepared by addition reaction of monomeric diisocyanates using specific catalysts (Laas, H. J.; Halpaap, R.; Pedain, J.; *J. prakt. Chemie* 336 (1994), 185-200). Apart from TDI uretdione, available for example as Desmodur® TT/G from Rhein-Chemie, it is preferred to use HDI uretdione, which is available commercially as Desmodur® N 3400 from BAYER. These compounds constitute commercial products, which are frequently not in pure form but instead represent mixtures of compounds of similar structure.

The monoalcohols used for compound A are aliphatic, cycloaliphatic and araliphatic alcohols. With regard to the aliphatic alcohols, linear, branched or cyclic alcohols of chain length $C_1$-$C_{22}$ are used, such as methanol, ethanol, n-propanol, 2-propanol, n-butanol, isobutanol, tert-butanol, hexanol, octanol, decanol, dodecanol, oleyl alcohol and stearyl alcohol. Glycol monoethers such as ethylene glycol monopropyl ether, ethylene glycol monobutyl ether, ethylene glycol mono(2-ethylhexyl ether) or ethylene glycol monophenyl ether, are likewise included. Cycloaliphatic alcohols include, for example, cyclopentanol and cyclohexanol. Araliphatic alcohols such as benzyl alcohol, for example, likewise find use. Representatives of the cyclic alcohols may include, for example, 1-(2-hydroxyethyl)imidazolidin-2-one. Polymeric alcohols such as polyolefin monools, polyacrylate monools, polycarbonate monools, polycaprolactone monools, polyoxazoline monools or polysiloxane monools are also included by the invention, as are fatty alcohol alkoxylates with variable degrees of alkoxylation, of the kind known to the skilled person under the trade name Lutensol from BASF. Preference is given to using polyoxyalkylene monoalcohols which contain ethylene oxide and/or propylene oxide and/or butylene oxide groups and where appropriate have been modified with styrene oxide. Particular preference is given to the use of polyoxyalkylene monoalcohols such as MPEG 350, MPEG 500 and MPEG 750, for example, which are polyoxyethylenes prepared starting from methanol and containing a terminal OH group. The monoalcohols can also be used in mixtures.

The monoamines used for preparing the uretdione-containing compound A are aliphatic, cycloaliphatic and araliphatic amines. With regard to the aliphatic amines, linear, branched or cyclic amines of chain length $C_2$-$C_{22}$ are used, such as ethylamine, propylamine, isopropylamine, butylamine, sec- and tert-butylamine, 3-methyl-1-butanamine, hexylamine, 2-ethylhexylamine, octylamine, cyclopentylamine, cyclohexylamine, tri-decylamine, oleylamine, octadecylamine and the mixtures of $C_{12}$-$C_{22}$ amines that are known under the trade name Armeen from Akzo Nobel. Amines in accordance with the invention are not only polyolefin amines such as polyisobutylenamine, for example, but also, preferably, polyoxyalkylene monoamines, which contain ethylene oxide and/or propylene oxide groups and which are known under the trade names Jeffamine® M 600, M 1000, M 2005 and M 2070 from Huntsman. The araliphatic amines are products such as benzylamine and furfurylamine, for example. It is also possible, however, to use hydrazides such as benzoic hydrazide, for example. The monoamines can also be used as mixtures, and it is also possible for the monoamines to be employed as a mixture with the monoalcohols and the monohydrazides, in any proportion.

It is likewise possible to use alkanolamines for preparing the uretdione-containing compound A. Examples that may be given here include 2-aminoethanol, 3-amino-1-propanol, 1-amino-2-propanol, 2-(2-aminoethoxy)-ethanol, diethanolamine, 3-(2-hydroxyethylamino)-1-propanol, diisopropanolamine, and compounds thereof that are alkoxylated on the OH groups.

The reaction between uretdione-containing polyisocyanate and the monoalcohol is carried out at temperatures between 15 and 90° C., preferably between 20 and 75° C., where appropriate with assistance of a catalyst, such as dibutyltin dilaurate (DBTL). The reaction between the uretdione-containing polyisocyanate and the monoamine, and/or the alkanolamine and/or the monohydrazide, is carried out at temperatures between 15 and 45° C., preferably between 20 and 30° C. The sequence of addition of the co-reactants is generally arbitrary; the uretdione-containing polyisocyanate is introduced initially, where appropriate in an inert solvent, and the monoalcohol, the monoamine, the alkanolamine or the monohydrazide is added dropwise. It is also possible for the monoalcohol, the monoamine, the alkanolamine or the monohydrazide to be introduced initially, with the uretdione-containing polyisocyanate added dropwise. Where component A contains not only urethane groups but also urea groups and/or semicarbazide groups, the uretdione-containing polyisocyanate is reacted first with the alcohol and thereafter with the amine and/or the monohydrazide. Where appropriate, the reaction can also be carried out in an inert solvent, such as methoxypropyl acetate, cyclohexane, toluene, xylene or a relatively high-boiling aromatic such as Shellsol A, for example.

The monoamine-functional compounds of the general formula (B)

$$H_2N-R^3-[Z-R^4-Z-R^5]_a-Z-R^6 \quad (B)$$

are prepared under conditions of the kind known to the skilled person, and are obtainable, for example, by reacting a mixture of monocarboxylic and polycarboxylic acids, preferably dicarboxylic acids, and/or dicarboxylic anhydrides, with diamines, preferably at temperatures from 100 to 250° C., more preferably 140 to 200° C., with water being separated off. The ratio of diamine to polycarboxylic acid to monocarboxylic acid is 3:2:1 to 20:19:1, more preferably 3:2:1 to 8:7:1. In one preferred embodiment, compounds of the general formula (B) can be prepared by first reacting the dicarboxylic acid and/or dicarboxylic anhydride with the diamine at temperatures from 100 to 250° C., more preferably 140 to 200° C., with water being separated off, to give a condensation product of the general formula (C)

$$H_2N-R^3-[Z-R^4-Z-R^5]_a-NH_2 \quad (C)$$

having an amine number of preferably 5 to 180 and more preferably 15 to 100, based on 100% active substance, and then, at temperatures from 100 to 250° C., more preferably 140 to 200° C., reacting compound (C) with the monocarboxylic acid, with water being separated off, to give compound (B), this condensation product having an amine number of preferably 3 to 80 and more preferably of 8 to 50, based on 100% active substance.

The diamines are preferably aliphatic, aromatic and araliphatic primary diamines, such as ethylenediamine, neopentanediamine, 1,2- and 1,3-propanediamine, 1,4-butanediamine, 1,5-pentanediamine, 2-butyl-2-ethyl-1,5-pentanediamine, 1,6-hexamethylenediamine (also as a solution in water), 1,8-octamethylenediamine, 1,12-dodecamethylenediamine, cyclohexyldiamine, 4,4'-diaminodicyclohexylmethane, 3,3'-dimethyl-4,4'-diaminodicyclohexylmethane, isophoronediamine, 4,7-dioxadecane-1,10-diamine, 4,11-dioxatetradecane-1,14-diamine, 4,7,10-trioxadecane-1,13-diamine, polyoxyalkylenediamines containing ethylene oxide and/or propylene oxide groups, arranged randomly or blockwise, possessing a number-average molecular weight of 148 to 4000 g/mol and being obtainable, for example, as Jeffamine® D 230, D 400, D 2000, D 4000 and Jeffamine® ED 600, ED 900, ED 2003 and EDR 148 from Huntsman, polytetrahydrofurandiamines such as bis(3-aminopropyl)-polytetrahydrofuran 350, 750, 1100 and 2100 (the numbers indicate the approximate molecular weight), 4,4'-diaminodiphenylmethane, 3,3'-diaminodiphenyl sulphone and para- and meta-xylylenediamine. Preference is given to using 1,6-hexamethylenediamine, 1,8-octamethylenediamine and meta-xylylenediamine. It is likewise possible to use amines of type $H_2N-R-NR-R-NH_2$, R standing independently for ($C_1$-$C_{18}$)-alkyl or ($C_1$-$C_4$)-alkoxy. One example thereof is N,N'-bis(3-aminopropyl)-methylamine. Use may also be made, however, of dihydrazides such as oxalic dihydrazide, succinic dihydrazide or adipic dihydrazide. The use of mixtures of the diamines, including mixtures with the dihydrazides, is likewise possible. The diamines can also be used as carbonate compounds, which in the condensation reaction react with the polycarboxylic acids, with the water being separated off and with $CO_2$ being eliminated, to form the inventively preferred amide moieties.

The polycarboxylic acids are preferably aliphatic, cycloaliphatic or aromatic, linear or branched, saturated or unsaturated dicarboxylic acids having at least 2, more preferably 3 to 40, C atoms. Examples of such polycarboxylic acids are adipic acid, oxalic acid, malonic acid, succinic acid, glutaric acid, pimelic acid, suberic acid, sebacic acid, azeleic acid, undecanedioic acid, 1,11-undecanedicarboxylic acid, dodecanedioic acid, hexadecanedioic acid, docosanedioic acid, maleic acid, fumaric acid, terephthalic acid or isophthalic acid, used alone or in mixtures. Acid anhydrides such as maleic anhydrides, glutaric anhydride, phthalic anhydride and succinic anhydride, which where appropriate are modified with alkyl or alkylene groups, such as dodecenylsuccinic anhydride, for example, are likewise included in the invention. Polymeric polycarboxylic acids such as the dicarboxylic acid of polybutadiene, for example, can also be used, as can hydroxy-functional polycarboxylic acids such as tartaric acid, citric acid and hydroxyphthalic acid, for example. Oxydicarboxylic acids such as 3,6,9-tri-oxyundecanedioic acid and polyglycol dioic acid are likewise included. Dimerized fatty acids, known to the skilled person as dimer acids, having a carbon length of 36 C atoms, are especially preferred. These dimer acids may have both a low monomer content (typically <8 per cent by weight) and also a fraction of not more than 25 per cent by weight of trimer acid.

The monocarboxylic acids are saturated, mono- to polyunsaturated, linear and branched aliphatic carboxylic acids such as, for example, acetic acid, propionic acid, butyric acid, isobutyric acid, valeric acid, isovaleric acid, caproic acid, oenanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotinic acid, melissic acid, lauroleic acid, myristoleic acid, palmitoleic acid, petroselinic acid, oleic acid, elaidic acid, vaccenic acid, erucic acid, linoleic acid, linolenic acid, arachidonic acid, clupanodonic acid, ricinenic acid, α-elaeostearic acid, α-parinaric acid, coconut oil fatty acid, palm kernel oil fatty acid, coconut/palm kernel oil fatty acid, palm oil fatty acid, cotton oil fatty acid, peanut oil fatty acid, soya oil fatty acid, sunflower oil fatty acid, rapeseed oil fatty acid and tallow fatty acid. Also used are ketocarboxylic acids such as licanic acid, for example, and aromatic monocarboxylic acids such as benzoic acid, for example. As representatives of the hydroxycarboxylic acids mention may be made, for example, of glycolic acid, 5-hydroxyvaleric acid, 6-hydroxycaproic acid, ricinol fatty acid, 12-hydroxystearic acid, 12-hydroxydodecanoic acid, 5-hydroxydodecanoic acid, 5-hydroxydecanoic acid or 4-hydroxydecanoic acid. Mixtures of the monocarboxylic acids can be used as well.

The monocarboxylic and/or polycarboxylic acids may be replaced in part by mono- and/or diisocyanates, and the diamines may be replaced in part by diols, in which case ester, urethane and/or urea groups may be present alongside the preferred amide moieties in the compounds of the general formulae (B) and (C).

The diols, alone or in mixtures, are preferably polyoxyalkylenediols, polyoxyalkenyldiols modified where appropriate with ($C_1$-$C_4$)-alkyl and/or -alkoxy groups, polyesterdiols, mixed polyester-polyoxyalkylenediols, polylactonediols, mixed polyoxyalkylene-polylactonediols, polycarbonatediols, polyolefindiols, polyacrylatediols, alkoxylated bisphenol A diols, diols of the α,ω-dihydroxyalkylenesiloxane type, and their alkoxylated compounds having an average molecular weight, $M_n$, of 250 to 5000 g/mol.

Diisocyanates used may be preferably aliphatic, cycloaliphatic and aromatic diisocyanates, or mixtures of these. Examples of such diisocyanates are 1,4-tetramethylene diisocyanate, 1,6-hexamethylene diisocyanate, 2,2,4-trimethyl-1,6-hexamethylene diisocyanate, 1,10-decamethylene diisocyanate, 1,4-cyclohexylene diisocyanate, p-phenylene diisocyanate, m-phenylene diisocyanate, 2,6-tolylene diisocyanate, 2,4-tolylene diisocyanate and mixtures thereof, p- and m-xylylene diisocyanate, 1,5-naphthylene diisocyanate, isophorone diisocyanate, 4,4'-diisocyanatodicyclohexylmethane, 3,3'-dimethyl-4,4'-bisphenylene diisocyanate, 3,3'-dimethyldiisocyanatodiphenylmethane, the isomer mixtures of 2,4'- and 4,4'-diisocyanatodiphenylmethane, and $C_{36}$ dimer diisocyanate.

To prepare the biuret compounds of the invention, of the general structure A-B, the uretdiones of the general formula A and the monoamine-functional compounds of the general formula B are reacted at a reaction temperature between 60 and 120° C., more preferably between 75 and 90° C. The ratio of components A and B in this case is chosen such that for 1 mol of compound A between 0.8 mol and 1.2 mol, preferably between 0.9 mol and 1.1 mol, more preferably 1 mol of compound B is used. The reaction can be carried out with or without solvent. Suitable solvents are all aliphatic, aromatic, protic and aprotic solvents such as methoxypropyl acetate, cyclohexane, toluene, xylene or relatively high-boiling solvents such as Shellsol A or Exxsol D 40, for example. N-Methylpyrrolidone or N-ethylpyrrolidone, and also alcohols such as ethanol, propanol, isobutanol or butyl glycol, are likewise suitable. The addition reaction may also be carried out in a polyether such as polypropylene glycol 600 (the number indicates the approximate molecular weight), for example, as solvent. Mixtures of solvents can be used as well.

The invention further provides for the use of the biuret compounds of the invention, of the general structure A-B, and of the biuret compounds of the general structure A-B that are obtained by the process of the invention, as rheology control additives, particularly in solvent-borne and solvent-free coating compositions based on binders such as, for example, polyurethanes (1K and 2K—1-component and 2-component), polyacrylates, polyester resins, alkyd resins and epoxy resins, PVC plastisols and PVC organosols, epoxy-based coatings and unsaturated polyester resins. Coating compositions may also be understood to include nail enamels, of the kind described for example in Patent U.S. Pat. No. 6,156,325.

The amount used of the biuret compounds of the invention, of the general structure A-B, is 0.05% to 5.0% by weight active substance, preferably 0.1% to 3.0% by weight active substance and more preferably 0.2% to 2.0% by weight active substance, based on the weight of the overall formulation.

Additionally provided by the invention are cured and uncured polymer compositions comprising one or more of the biuret compounds of the invention, of the general structure A-B, or of the biuret compounds of the general structure A-B that are obtained by the process of the invention.

Below, the invention is elucidated further with reference to examples.

Preparation of Inventive Component A:

EXAMPLE 1

A 1-liter 3-necked flask with stirrer, reflux condenser and thermometer is charged at room temperature with 195.0 g (0.5 mol) of hexamethylene diisocyanate uretdione (Desmodur® N3400 from Bayer, NCO content=21.5%) and 138.2 g (1.0 mol) of ethylene glycol monophenyl ether and this initial charge is heated to 70° C. The reaction is carried on until the NCO content is less than 0.1%. The reaction mixture is then cooled to 50° C.

TABLE 1

| Components A: | | |
|---|---|---|
| Example | Uretdione | Amine/alcohol components |
| 2 | Hexamethylene diisocyanate uretdione | Decanol |
| 3 | Hexamethylene diisocyanate uretdione | Oleyl alcohol |
| 4 | Hexamethylene diisocyanate uretdione | Polyglycol M 350 |
| 5 | Hexamethylene diisocyanate uretdione | Benzylamine |
| 6 | Hexamethylene diisocyanate uretdione | Tridecylamine |
| 7 | Hexamethylene diisocyanate uretdione | Jeffamine ® M 600 |
| 8 | Hexamethylene diisocyanate uretdione | Jeffamine ® M 1000 |
| 9 | Hexamethylene diisocyanate uretdione | Polyglycol M 500/ tridecylamine (1:1 ratio) |

Key 1:
Jeffamine ® M 600: monoamine-functional EO/PO polyether (EO:PO = 1:9), Mn ~ 600 g/mol, from Huntsman
Jeffamine ® M 1000: monoamine-functional EO/PO polyether (EO:PO = 19:3), Mn ~ 1000 g/mol, from Huntsman
Polyglycol M 350, 500: monohydroxy-functional EO polyethers prepared starting from methanol, Mn ~ 350 or 500 g/mol from Clariant Preparation of Inventive Component B:

EXAMPLE 10

A 1-liter three-necked flask with stirrer, water separator and thermometer is charged in succession with 227.8 g (0.4 mol) of dimer acid Pripol™ 1009 (dimerized fatty acid, hydrogenated, Uniqema, max. 1% trimer acid), 69.6 g (0.6 mol) of hexamethylenediamine and 152.1 g of Exxsol D40 (dearomatized hydrocarbon, ExxonMobil Chemical) and this initial charge is heated slowly to 170° C. The water released slowly during the reaction is separated off azeotropically via the water separator. The condensation product has an amine number of 51. Subsequently 57.6 g (0.2 mol) of tall oil fatty acid (mixture of monocarboxylic acids containing a high level of oleic and linoleic acid and about 2% resin acids (abietic acid), Arizona Chemical GmbH) are added and the water released during this reaction is separated off azeotropically via the water separator. This condensation product has an amine number of 22.7. Thereafter the reaction mixture is cooled to 50° C.

TABLE 2

Components B:

| Example | Diamine a | Dicarboxylic acid b | Mono-carboxylic acid c | Molar ratio a:b:c |
|---|---|---|---|---|
| 11 | Hexamethylene-diamine | Pripol ™ 1006 | Tall oil fatty acid | 6:5:1 |
| 12 | Hexamethylene-diamine | Pripol ™ 1009 | Heptanoic acid | 7:6:1 |
| 13 | Hexamethylene-diamine | Pripol ™ 1013 | 12-Hydroxy-stearic acid | 5:4:1 |
| 14 | Octamethylene-diamine | Empol ® 1062 | Stearic acid | 3:2:1 |
| 15 | m-Xylylene-diamine | Pripol ™ 1017 | Tall oil fatty acid | 6:5:1 |
| 16 | Jeffamine ® ED 600 | Adipic acid | Stearic acid | 4:3:1 |
| 17 | Jeffamine ® D 230 | Adipic acid/ Pripol ™ 1006 1:2 ratio | Tall oil fatty acid | 5:4:1 |
| 18 | Hexamethylene-diamine | Pripol ™ 1006 | Acetic acid | 3:2:1 |
| 19 | Hexamethylene-diamine/ m-xylylene-diamine (2:3 ratio) | Empol ® 1012 | Oleic acid | 4:3:1 |

Key 2:
Pripol ™ 1006: dimerized fatty acid (max. 4% trimer acid), hydrogenated, from Uniqema
Pripol ™ 1009: dimerized fatty acid (max. 1% trimer acid) hydrogenated, from Uniqema
Pripol ™ 1013: dimerized fatty acid (max. 4% trimer acid), from Uniqema
Pripol ™ 1017: dimerized fatty acid (max. 22% trimer acid), from Uniqema
Empol ® 1062: dimerized fatty acid (max. 3.5% polycarboxylic acid), partly hydrogenated, from Cognis
Empol ® 1012: dimerized fatty acid (max. 5% polycarboxylic acid), hydrogenated, from Cognis
Jeffamine ® ED 600: diamine-functional EO/PO polyether (EO:PO = 9:3.6), Mn ~ 600 g/mol, from Huntsman
Jeffamine ® D 230: diamine-functional PO polyether, Mn ~ 230 g/mol, from Huntsman Preparation of Inventive Biuret Adducts:

EXAMPLE 20

A 1-liter 3-necked flask with stirrer, reflux condenser and thermometer is charged in succession at room temperature with 66.6 g (0.1 mol) of the adduct from Example 1 and 247.1 g (0.1 mol; amine number=22.7) of the condensation product from Example 10 and this initial charge is heated to 85° C. The reaction mixture is stirred until the amine number is less than 1. Then the product is diluted with isobutanol to a solids of 30%.

TABLE 3

Biuret adducts:

| Example | Component A | Component B |
|---|---|---|
| 21 | Example 2 | Example 19 |
| 22 | Example 4 | Example 11 |
| 23 | Example 7 | Example 15 |
| 24 | Example 8 | Example 13 |
| 25 | Example 9 | Example 14 |

Performance Results:
White paint formula: Worléekyd S 365 white paint, 64% binder, 20% TiO2

| | |
|---|---|
| Worléekyd S 365, 70% in K 030 | 34.4 |
| Disperbyk ® 110 | 0.6 |
| RKB-2 (TiO$_2$) | 20.0 |
| BYK 066 | 0.3 |

Dispersion: 30 min. Dispermat, 50° C., 8500 rpm, 4 cm Teflon disc

| | |
|---|---|
| Nuodex Combi APB | 4.5 |
| Borchi Nox M2 | 0.2 |
| K 030 | 10.4 |
| | 100 |

Key 3:
Worléekyd S 365: long-oil alkyd resin, air-drying, from Worlée
Disperbyk ® 110: wetting and dispersing additive (solution of a copolymer containing acidic groups) from BYK-Chemie
RKB-2: white pigment (titanium dioxide) from BAYER AG
BYK 066: silicone defoamer from BYK-Chemie
Nuodex Combi APB: combination dryer from Sasol Servo BV
Borchi Nox M2: anti-skinning agent (methyl ethyl ketoxime) from Borchers
K030: mixture of paraffinic, naphthenic and aromatic hydrocarbons in the $C_8$-$C_{11}$ range, from Solvadis Deutschland Additive dosage: 1% by weight active substance, based on the weight of the overall composition
Incorporation: add additive with stirring with the Dispermat, toothed disc 2.5 cm, 1200 rpm, 2 min.
Assessment: testing of the rheological activity in the form of the sag limit:
for this purpose the additized paint systems are applied using the stepped coater 50-500 μm and 550-1000 μm to BYK Gardner 2801 contrast charts, using an automatic applicator from BYK Gardner (rate: 3 cm/sec). The contrast charts are dried hanging vertically. The stability is read off wet in μm. This is a measure of the rheological activity. The results are set out in Table 4.

TABLE 4

| Additive | Sag limit [μm] |
|---|---|
| Control (no additive) | 150 |
| BYK 411 | 450 |
| Example 20 | 900 |
| Example 21 | 550 |
| Example 22 | 800 |
| Example 23 | 650 |
| Example 24 | 1000 |
| Example 25 | 750 |

Key 4:
BYK 411: liquid rheological additive from BYK-Chemie

The invention claimed is:

1. A biuret compound of the general formula

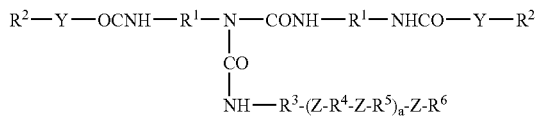

in which
- $R^1$ is a $(C_1-C_{22})$-alkylene, $(C_3-C_{22})$-alkenylene, $(C_5-C_{15})$-cycloalkylene, arylene, $(C_7-C_{12})$-aralkylene, a polyoxyalkylene radical or is a polyester radical,
- $R^2$ is a $(C_1-C_{22})$-alkyl, hydroxy-$(C_1-C_{22})$-alkyl, $(C_3-C_{18})$-alkenyl, aryl, $(C_7-C_{12})$-aralkyl, or $(C_5-C_{12})$-cycloalkyl radical, a hydroxy-, $(C_1-C_{22})$-alkoxy-, $(C_5-C_{12})$-cycloalkoxy-, or $(C_7-C_{12})$-aralkoxy-polyoxyalkylene radical, or a polyester radical prepared starting from a $(C_1-C_{22})$-alkanol, $(C_5-C_{12})$-cycloalkanol, or $(C_7-C_{12})$-aralkanol or from a $(C_1-C_{22})$-alkoxy-, $(C_6-C_{12})$-cycloalkoxy-, or $(C_7-C_{12})$-aralkoxy-polyoxyalkylene,
- Each Y is independently selected from the group consisting of O, NH, CO—NH—NH and NH—NH—CO,
- $R^3$, $R^4$ and $R^5$ independently of one another are a $(C_2-C_{40})$-alkylene, $(C_3-C_{40})$-alkenylene, $(C_5-C_{40})$-cycloalkylene, arylene, $(C_7-C_{40})$-aralkylene or polyoxyalkylene radical or are a polyester radical,
- $R^6$ is a $(C_1-C_{30})$-alkyl, $(C_3-C_{22})$-alkenyl, hydroxyalkyl and hydroxyalkenyl, $(C_4-C_{13})$-cycloalkyl, aryl or $(C_7-C_{12})$-aralkyl radical,
- Each Z is independently selected from the group consisting of COO, OCO, NHCO, CONH, NHCOO, OOCNH and NHCONH, and
- a is a number from 1 to 19.

2. A biuret compound according to claim 1, wherein $R^1$ is a hexamethylene radical.

3. A biuret compound according to claim 1 wherein $R^2$ is a $(C_1-C_{22})$-alkyl or a -alkoxypolyoxyalkylene radical.

4. A biuret compound according to claim 1, wherein the radicals $R^3$ and $R^5$ independently of one another are a $(C_2-C_{18})$-alkylene or $(C_7-C_{15})$-aralkylene radical.

5. A biuret compound according to claim 4 wherein the radicals independently are a $C_2-C_{12}$-alkylene or a $(C_7-C_{12})$-aralkylene radical.

6. A biuret compound according to claim 4 wherein the radicals independently are a $(C_2-C_8)$-alkylene or a $(C_7-C_9)$-aralkylene radical.

7. A biuret compound according to claim 4 wherein the radicals independently are a hexamethylene, octamethylene or m-xylylene radical.

8. A biuret compound according to claim 1, wherein the radical $R^4$ is a $(C_2-C_{40})$-alkylene, $(C_3-C_{40})$-alkenylene, $(C_5-C_{40})$-cycloalkylene, arylene or $(C_7-C_{40})$-aralkylene radical.

9. A biuret compound according to claim 8 wherein the radical is a $(C_{30}-C_{40})$-alkylene, $(C_{30}-C_{40})$-alkenylene, $(C_{30}-C_{40})$-cycloalkylene, arylene or $(C_{30}-C_{40})$-aralkylene radical.

10. A biuret compound according to claim 1, wherein at $R^6$ is a $(C_1-C_{30})$-alkyl or a $(C_3-C_{22})$-alkenyl radical.

11. A biuret compound according to claim 1, wherein Z is NHCO or CONH.

12. A biuret compounds according to claim 1, wherein a is equal to 2 to 7.

13. A composition comprising a mixture of biuret compounds wherein each biuret compound of the mixture is a biuret compound according to claim 1.

14. A process for preparing a biuret compound according to claim 1, comprising reacting a uretdione of the general formula (A)

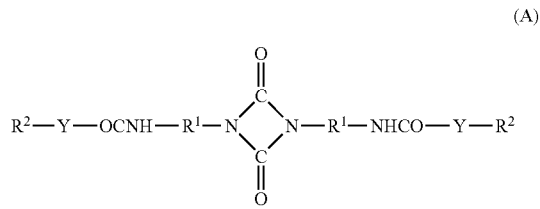

where $R^1$ is a $(C_1-C_{22})$-alkylene, $(C_3-C_{22})$-alkenylene, $(C_5-C_{15})$-cycloalkylene, arylene, $(C_7-C_{12})$-aralkylene, a polyoxyalkylene radical or is a polyester radical, $R^2$ is a $(C_1-C_{22})$-alkyl, hydroxy-$(C_1-C_{22})$-alkyl, $(C_3-C_{18})$-alkenyl, aryl, $(C_7-C_{12})$-aralkyl, or $(C_5-C_{12})$-cycloalkyl radical, a hydroxy-, $(C_1-C_{22})$-alkoxy-, $(C_5-C_{12})$-cycloalkoxy-, or $(C_7-C_{12})$-aralkoxy-polyoxyalkylene radical, or a polyester prepared starting from a $(C_1-C_{22})$-alkanol, $(C_5-C_{12})$-cycloalkanol, or $(C_7-C_{12})$-aralkanol or from a $(C_1-C_{22})$-alkoxy-, $(C_6-C_{12})$-cycloalkoxy-, or $(C_7-C_{12})$-aralkoxy-polyoxyalkylene, and Each Y is independently selected from the group consisting of O, NH, CO—NH—NH or NH—NH—CO, with at least one monoamine-functional compound of the idealized general structure (B)

where $R^3$, $R^4$ and $R^5$ independently of one another are a $(C_2-C_{40})$-alkylene, $(C_3-C_{40})$-alkenylene, $(C_5-C_{40})$-cycloalkylene, arylene, $(C_7-C_{40})$-aralkylene or polyoxyalkylene radical or are a polyester radical, $R^6$ is a $(C_1-C_{30})$-alkyl, $(C_3-C_{22})$-alkenyl, hydroxyalkyl and hydroxyalkenyl, $(C_4-C_{13})$-cycloalkyl, aryl or $(C_7-C_{12})$-aralkyl radical, Each Z is independently selected from the group consisting of COO, OCO, NHCO, CONH, NHCOO, OOCNH and NHCONH, and a is a number from 1 to 19.

15. A rheology control agent comprising the biuret compound according to claim 1 or a mixture thereof.

16. A thixotropic coating system comprising a coating composition of at least one binder, an optional solvent and one or more biuret compounds according to claim 1.

17. A thixotropic coating system according to claim 16 wherein the biuret compounds function as anti-sag agents and/or anti-settling agents.

* * * * *